(12) United States Patent
Miwa et al.

(10) Patent No.: US 6,450,979 B1
(45) Date of Patent: Sep. 17, 2002

(54) ULTRASONIC WAVE IRRADIATION APPARATUS

(75) Inventors: Hirohide Miwa, Kawasaki; Masato Kino, Tokyo, both of (JP)

(73) Assignee: Miwa Science Laboratory Inc., Kanagawa (JP)

( * ) Notice: Subject to any disclaimer, the term of this patent is extended or adjusted under 35 U.S.C. 154(b) by 0 days.

(21) Appl. No.: 09/600,177

(22) PCT Filed: Nov. 9, 1998

(86) PCT No.: PCT/JP98/05032

§ 371 (c)(1),
(2), (4) Date: Aug. 4, 2000

(87) PCT Pub. No.: WO99/39677

PCT Pub. Date: Aug. 12, 1999

(30) Foreign Application Priority Data

Feb. 5, 1998 (JP) .................................. PCT/JP98/00487

(51) Int. Cl.[7] .............................. A61H 1/00; A61H 1/02; A61H 5/00
(52) U.S. Cl. ............................... 601/2; 604/22; 600/439
(58) Field of Search .............................. 601/2; 604/22; 600/437, 438

(56) References Cited

U.S. PATENT DOCUMENTS 4,791,915 A * 12/1988 Barsotti et al. ............... 128/24
5,879,314 A * 3/1999 Peterson et al. ............... 601/2
6,126,619 A * 10/2000 Peterson et al. ............... 601/2
6,190,315 B1 * 2/2001 Kost et al. ................... 600/309

OTHER PUBLICATIONS

Masuda, "Wrinkles Stretched in Only 5 Minutes," Success Marketing Co., Ltd. (Aug. 25, 1996), pp. 79–83, 112–19, 132–33 and 36.
*Note: identified relevant portions of document are discussed in the present specification, pp. 2–3.

* cited by examiner

Primary Examiner—Marvin M. Lateef
Assistant Examiner—Jeoyuh Lin
(74) Attorney, Agent, or Firm—Paul A. Guss (57) ABSTRACT

This invention discloses an equipment for lipolysis of fat of a living body by ultrasound sonication. An effective ultrasound is characterized in low frequency 15–140 kHz region, by an intensity when in a range of 15–50 kHz, which is greater than 10 mw/cm$^2$ and below a hemolysis limit, and an intensity when in a range of 50–140 kHz, which is greater than 4 mW/cm$^2$ and below the hemolysis limit or the safety level defined by MI. The invention is further characterized in a high frequency 180–1.3 MHz region, by an intensity when in a range of 180–700 kHz, which is greater than 10 mw/cm$^2$ and below the safety level defined by M.I, and the intensity when in a range of 700 kHz–1.3 MHz, which is greater than 800 mw/cm$^2$ and below the safety level defined by MI.

13 Claims, 7 Drawing Sheets

ULTRASONIC WAVE IRRADIATION APPARATUS

TECHNOLOGICAL FIELD

The present invention belongs to the field of equipment for reduction and prevention of obesity, and improvement of obesity for health and beauty, especially relating to ultrasound equipment for medical treatment and prevention of obesity and improvement of obesity for health and beauty.

BACKGROUND ART

Recently adult (including Mammalian) diseases such as diabetes mellitus, hypertension, and vascular degeneration of brain and viscera have become serious problems. Their greatest origin is obesity.

For improvement of obesity, it is known scientifically that suppression of caloric intake and exercise are effective. Administration of appetite suppressers and digestion/intake suppressers in addition to thermo-metabolism enhancers are under study and some of them are approved by the Government.

As for exercise, persons tend to undertake dieting, walking, physical exercise, dancing, swimming, cycling, etc, due to a shortage of exercise resulting from sedentary occupations and the popularization of automobiles. However, it is a big problem that maintaining an exercise program is very difficult without ample time and strong will. Therefore, a method for reducing obesity comfortably and effectively is desired.

There are some aesthetic salons in the market which are announcing fat reduction by ultrasound as a variation of folk medicine. But such techniques have no scientific evidence, the used frequency of all the equipment is 1 MHz, and there is no display of acoustic intensity, but only an electric input power per transducer unit area. For example, the book titled "Wrinkles Stretched in only 5 min." by Masuda, published on Aug. 25, 1996 by Success Marketing Co. Ltd. discloses an ultrasound treatment method using an ultrasound applicator for beauty, increased blood flow and lymphoid flow, by the effect of thermo-heating and massage, for enhancing beauty of the skin. Such thermo-heating brings the fat to an easily decomposable state and massage further promotes such decomposing. Stimulation, by ultrasound, of the sensitive spot known as "tubo in acupuncture and moxibustion is also disclosed. In the aforesaid book, 1–10 MHz for medical treatment and 1 MHz for beauty enhancement are disclosed. In relation to the sonicating acoustic power density, or intensity, the following facts are disclosed: The safety limit defined by the Society for Ultrasound for Medicine and Biology is 1000 mW/cm$^2$ for continuous wave (CW) sonication and 240 mW/cm$^2$ (SPTA) for pulse wave (PW) sonication. For beauty enhancing applications, the intensity used was 1500–2000 mW/cm$^2$ for thick muscles, 1000–1500 mW/cm$^2$ for thin muscles, 500 mW/cm$^2$ for the face in CW sonication and 120 mW/cm$^2$ for the face in PW sonication. And their level is half of the aforesaid safety limit.

However, the intensity used for the thick and thin muscles disclosed above clearly exceeds the safety limit of 1000 mW/cm$^2$ for CW, so the disclosed intensity must be the electric power per transducer unit area. If we assume they are of electric power intensity, then an electric intensity of 1500–2000 mW/cm$^2$ corresponds to 500–700 mW/cm$^2$ of acoustic intensity, as the electric to acoustic conversion efficiency of the transducer is usually 30% and coincides with the description that they are half the safety limit. In another chapter it is disclosed that a scientific experiment on reduction of fat was carried out and the reduction was effective, and a reduction amount is reported. Although a scientific description of the sonication conditions such as intensity is not shown, it is reasonably presumed in context with the nearby sentences that 1 MHz of the equipment for beauty enhancement was used, and that its acoustic intensity was less than 700 mW/cm$^2$ again considering the aforesaid electric to acoustic conversion efficiency.

Concerning patent applications, Tokukai Hei-4-89058 (Yahmann Co) discloses an equipment for beauty using a frequency of 1–3 MHz and an intensity of 100–500 mW/cm$^2$. Tokukai Hei 3-123559 (Yahmann Co.) discloses a fat reducing effect which is introduced by muscle shrinkage and an improvement in blood /lymphoid liquid flow. In the detailed explanation of this specification, a frequency of 20–50 KHz, and an intensity of 100–500 mW/cm$^2$ is disclosed, but there is no disclosure of any scientific reason why these values are specified, nor any scientific data explaining what the specified values are based on. Further, no commercialized product has yet appeared on the market.

The specified values 20–50 KHz at 100–500 mW/cm$^2$ and 1–3 MHz at 100–500 mW/cm$^2$ in the prior art, do not have any scientifically provable data attesting to their effectiveness. Further, the reasons why these values are specified, taking safety into consideration, have not been described. According to the experiments carried out and described later by the inventor, these values are inadequate.

An object of the present invention is to clarify the effective frequency and intensity, including safety considerations, for lipolysis of living bodies, as well as providing equipment for performing lipolysis of a living body safely and effectively using ultrasound sonication.

DISCLOSURE OF INVENTION

In a living body, fat is synthesized by lipo-synthesizing enzymes in the adipocyte from glucose and free fat acid, and forms an oil droplet. As for humans, adipocyte of adults is mostly white adipocyte. So, hereafter, adipocyte shall be taken to imply white adipocyte. Adipocyte is slender and 20 $\mu$m in length at birth but grows to a 100 $\mu$m (sometimes 200 $\mu$m) diameter sphere in accordance with fat accumulation.

The accumulation of fat in adults is caused by the growth of each adipocyte rather than an increase in their number. In a grown adipocyte, the oil droplet is covered by a water based cell liquid layer, the thickness of which is much less than the diameter of the oil droplet itself.

In the cell liquid, there is enclosed an endoplasmic reticulum, which includes a lipolytic enzyme referred to as hormone sensitive lipase (HSL), which decomposes the fat into glycerol and fatty acid. Meanwhile., the fat oil droplet surface is covered with a flowable molecular layer of phospholipid and is protected from contact with the lipolytic enzyme located on the endoplasmic reticulum surface.

In the fat of the living body, the phospholipid layer partly disappears when hormones, such as epinephrine (adrenaline) released from adorenal modula or norepinephrine (noradorenarine) released from sympathetic nerve, are introduced. Then the oil drop makes contact directly with the endoplasmic reticulum and lipolysis starts. Fat is resolved into glycerol and free fatty acid, and the resolved products exit from the cell into the blood and are finally burned or consumed by exercise etc. The remaining final products are discharged from the body as $CO_2$ and $H_2O$ in expiration and/or urine.

It is known that ultrasound sonication on a living body has effects such as the promotion of enzyme reactions, emulsification, thermogenic effects, expansion of capillary blood vessels, and enhancement of metabolism. In the present invention, the increase of peripheral blood flow by expansion of the capillary blood vessels as a result of sonication is the same as in the prior art equipment used for health and beauty. However, the inventors have doubts about the lack of scientific evidence for the effectiveness of such conventional equipment for health and beauty and the frequencies used for them. As predicted from the aforesaid biochemical mechanisms of lipolysis, there must be an effective frequency less than 1 MHz, and the effectiveness must be frequency dependent, for such mechanisms as the stimulation of sympathetic nerves, the release of hormones at their ends, and activation and fluidization of the phospholipid layer. The inventors have confirmed the effective frequency and its intensity experimentally to examine this prediction. The present invention is based on the fact that the results obtained by such experimentation are quite different from the descriptions in the prior art.

According to the invention, a reasonable explication is as follows. The end of the sympathetic nerve is stimulated by sonication at a specific frequency and intensity which releases a hormone for lipolysis such as norepinephrine (noradorenarine), or the phospholipid layer or oil drop itself may be agitated and some contact occurs between the oil drop and the endoplasmic reticulum, namely a lipolysis enzyme, and thus, lipolysis occurs.

A first aspect of the present invention is an ultrasound sonication equipment, providing an ultrasound generation means for treating a living body with the generated ultrasound to thereby cause lipolysis of fat in the living body, specifically characterized by an ultrasound energy of 15–140 KHz, and wherein the intensity at the sonicated body surface is greater than 10 mW/cm$^2$ and below the hemolysis safety limit when the ultrasound energy is between 15–50 kHz, and greater than 4 mW/cm$^2$ and less than the hemolysis limit or the safety limit defined by the Mechanical Index when the ultrasound energy is between 50–140 kHz.

A second aspect of the present invention is an ultrasound sonication equipment, providing an ultrasound generation means for treating a living body with the generated ultrasound to thereby cause lipolysis of fat in the living body, specifically characterized by an ultrasound energy of 180 KHz–1.3MHz, and wherein the intensity at the sonicated body surface is greater than 10 mW/cm and below the safety limit defined by the Mechanical Index when the ultrasound energy is between 180–700 kHz, and is greater than 800 mW/cm$^2$ and below the safety limit defined by the Mechanical Index when the ultrasound energy is between 700 kHz–1.3 Mhz.

In the ultrasound sonication equipment according to the first and second aspects, the allowable maximum intensity is set below the level of no hemolysis or the safety level of Mechanical Index, but preferably is set below the level of no hemolysis or the safety level for medical diagnostic equipment.

Further, the equipments according to the first and second aspects are characterized by an intensity safety level which is set depending on the frequency for the Mechanical Index (MI): MI=0.6. The sonication can be any of continuous, pulsed, or intermittently generated, or a combination of such sonications. Intermittent sonication can be used to separate the time for forming the contact of the oil droplet with an enzyme, from the time in which fat is resolved after such contact.

Meanwhile, from a view point of health, it is not desirable for sonication to be performed carelessly. The safety level for medical diagnostic equipment is set at 1000 mW/cm$^2$ in the standard of the Society for Ultrasound in medicine and Biology, and by the FDA in the U.S.A., and this value can be described as applicable for a frequency range of 1–10 MHz. In this region, the intensity attenuation with penetration through the living body is strong, and the effective depth is limited to a shallow region beneath the body surface.

Here, the "effective depth is defined as the depth from the body surface, where lipolysis occurs effectively by sonication.

The energy given to the body is proportional to the intensity and time of the sonication. Penetration intensity decreases following an exponential function with the penetrated path length, where the exponent is given by a product of an absorption coefficient x length. Further, the absorption coefficient in the living body is proportional to the applied frequency. For example, the absorption coefficient divided by the frequency in human fat is 0.063 neper/cmMHz. So, the attenuation/absorption coefficient for penetration of 1 cm of fat is 0.55 dB/cm for 1 MHz and 1.09 dB/cm for muscle.

According to the inventor experiments, the effective intensity range for lipolysis was as wide as 10–1000 mW/cm$^2$ at a frequency of 500 kHz. And its effectiveness was constant for the widely spread intensity ranges. The effective depth can be calculated from the data as 135 cm for fat and 70 cm for muscle. In other words, the aforesaid intensity of 500 kHz can cause lipolysis still at deep viscera fat even after being attenuated to as low as 10 mW/cm$^2$, but such a low intensity never produces effects on bone and viscera.

On the other hand, the effective depth at 1 MHz is calculated as 1.7 cm for fat and 0.9 cm for muscle from the effective range of 800–1000 mW/cm$^2$, obtained by the experiment.

Again, the World Federation for Ultrasound in Medicine and Biology (WFUMB) introduced a concept of a Mechanical Index (MI) to estimate the risk of tissue destruction due to the mechanical cavitation. The MI is given by the following equation MI=P/f$^{1/2}$, wherein P is the maximum negative peak pressure in units of Mpa, and f is frequency in units of MHz.

The allowable level of the MI is not clearly defined and is left to the medical doctor discretion while compromising benefit and risk. However, some descriptions in which MI=0.6 or less are seen in medical treatment as safe. The Japanese Society for Ultrasound in Medicine has defined that MI should be less than 1. The present inventors have employed MI=0.6 as a limit, even though the limit may be altered in the future. This level can be applied for persons suffering from diseases of obesity and diseases whose origins lie in obesity. For undefined healthy individuals seeking applications for health and beauty enhancement, a level for medical diagnostic application of 1000 mW/cm$^2$ is recommended.

At a frequency of less than 1 MHz which is to be expected for biochemical fat reduction, ultrasound energy has strong penetration ability as well as a strong biochemical reaction. So, the influence on bone, blood vessel and viscera must be carefully considered.

Especially, in a range less than 100 kHz, dominant cavitation may pose a risk of tissue destruction and some stick tick feeling, even in the safer lower region, can be felt as uncomfortable. Further, hemolysis is easily produced by large emulsifying or dispersion forces. These actions are also functions of frequency and intensity. So, the intensity level should be below the aforesaid hemolysis limit.

Further, the FUMB noticed that care should be taken in regards to the tissue temperature under sonication, including such wider applications as medical treatment due to a thermal heating effect of sonication, and introduced the concept of s Thermal Index (TI) as a measure of the rise in temperature caused by sonication. A temperature elevation of less than 1.5° C. (TI<1.5) is quite safe in long term sonication, whereas 2° C. for 30 min. or 4° C. for 5 min. must be used under great caution.

Accordingly, the equipment according to the present invention includes a monitoring means for monitoring the location and temperature of the part of the body undergoing sonication. The ultrasound sonication equipment according to the invention provides a monitoring means which can perform such functions as determining the internal structure of the part of the body undergoing sonication, confirming the area undergoing sonication, determining an intensity level, calculating a time-integrated sonicated amount, and monitoring of the temperature rise caused by such sonication. Thus, it is possible to perform sonication while monitoring temperature elevation, while focusing on a specific viscerum and its vicinity, and avoiding exposing specific bones or viscerum to sonication. Hence, a safe and effective sonication can be realized.

In the ultrasound sonication equipment of the present invention, a sound energy transmitting means (applicator) is provided which generates ultrasound by the aforesaid means through an acoustic conducting medium. As such a medium, water, a bag containing water or liquid inside, and a non-liquid sound coupler etc., can be used. As the applicator (sound energy transmitting means), a bath or water box having the aforesaid ultrasound generator therein and a sound conducting medium like water, or a probe-like ultrasound applicator having the aforesaid ultrasound generator and a sound conducting bag containing a medium such as water or a non-liquid sound coupler etc. can be used. In the ultrasound sonication equipment of the present invention, the aforesaid ultrasound applicator provides an acoustic coupling layer between the applicator and the surface of the body. If an air layer exists between the applicator and the body surface, ultrasound is reflected by the air layer and cannot enter into the body. Therefore, interposing a coupling agent between the applicator and the body surface is used to avoid loss due to reflection and secures a positive sonication on the body. Such a coupling agent can be of any substance which acts to exclude air, such as a jelly or cream.

The coupling agent can also contain obesity reducing substances. By mixing percutaneous ointment with the coupling agent, or using the ointment itself as the coupling agent, a substance combining obesity reduction and acoustic coupling can be offered. Such combinations offer synergistic effects on fat reduction.

As a further aspect, the sound applicator can be one which provides a water flow for carrying ultrasound onto the surface of the body. For example, a shower head containing an ultrasound generator therein and which provides water or flows of warm water jets onto the body can be used, thereby generating the water flow jets carrying ultrasound therein, and used for sonication on the body. In another example, explained hereafter, the ultrasound generator is equipped in a bath and the warm water flow carrying ultrasound therein is generated and circulated in the bath. Then, the flow delivers ultrasound to the body. These examples disclose such applicators for a comfortable, labor free and easily operable sonication.

The substances which are decomposed by the aforesaid procedures, such as FFA, are released into the blood. It is necessary to burn or consume them by exercise or elevation of body temperature because, otherwise, they will be synthesized again into fat.

Therefore, in the present invention, the equipment can provide an obesity reducing agent together with the aforesaid sonication. Such an agent can be of percutaneous or oral administration, or can be administered by injection. For example, a food such as mustard, or medicines such as capsaicin, capsaicinoids or sibutramine, which elevate one's body temperature and enhance thermogenesis, can be taken or administered. Such a rise in body temperature, in the long term, tends to increase thermal radiation towards the outside of the body and thereby enhances the burning of FFA, etc.

Thereby, a synergistic effect, such as localized fat reduction, can be obtained by the combination of sonication and administration of the aforesaid obesity reduction agents. The combination can prevent fat from shifting from other parts of the body to the site which has been sonicated and reduced in fat.

The ultrasound sonication equipment of the present invention can provide a cooling means to cool at least a part of the body. If a part of the body is cooled, thermal energy is removed and a thermogenetic function due to homeostasis of the living body works autonomously to keep one's body temperature constant by the consumption or burning of FFA.

Such cooling means can comprise the aforementioned sound conducting medium, which has been cooled and prepared for contact with the body. If a controlling means to keep the temperature of the aforesaid sound conducting medium is kept at a temperature 24° C. cooler than body temperature, the body's own thermal energy is taken away, since any homeothermal animal generates autonomic thermogenesis.

THE PREFERRED EMBODIMENTS OF THIS INVENTION

The inventors of the present invention investigated at first the maximum intensity for the aforesaid hemolysis, cavitation, cell destruction and emulsification in order to confirm their safety. However, there is no well-approved method in the art for measuring absolute acoustic power. The only available method is to use weight balance. The equipment currently available is applicable above 800 kHz. The reason for inability below 800 kHz is due to the lack of an efficient absorbing material at such a low frequency to be lined inside of the measuring bath, and thereby standing waves are formed and reflected waves from the bath wall are inevitable. The inventors, after wide investigation, discovered an attenuating material which works in such a low frequency region, and by additionally lining the wall with the material, made it possible to measure intensity in such a low frequency region with certain accuracy. The aforesaid maximum intensity was measured with continuous waves and at frequencies of 24 kHz, 36 kHz, 100 kHz, 160 kHz, 500 kHz and 1 MHz.

Figure 1:
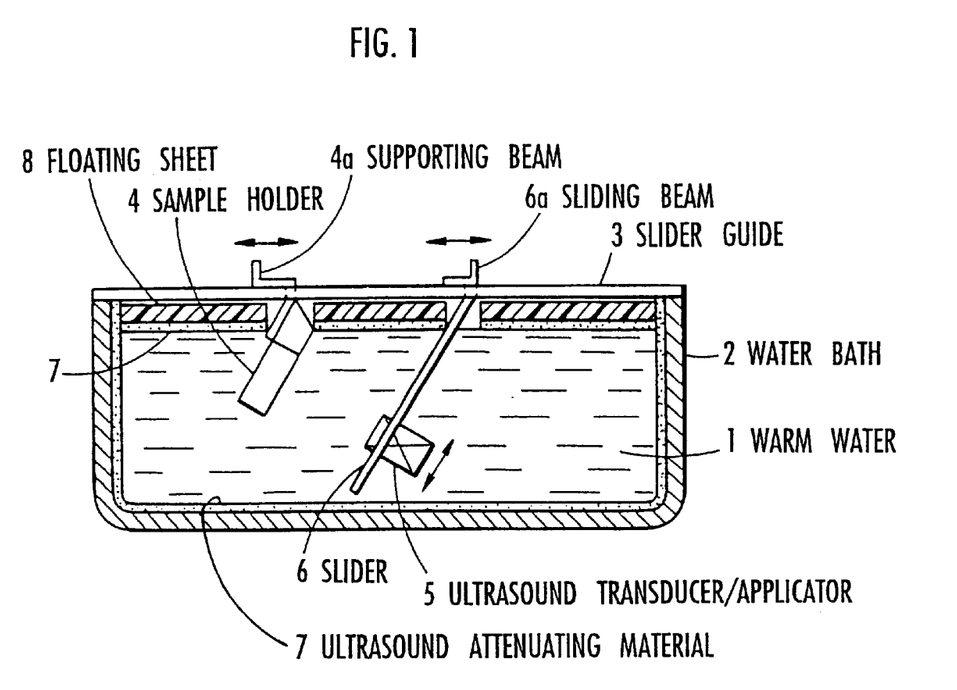
FIG. 1 is an illustrative cross-sectional view of the equipment used in an experiment to determine the effective region in frequency and intensity domain.

FIG. 1 shows the equipment used in the experiment for the aforesaid hemolysis. A slider-guide 3 is disposed on an upper level of the bath containing warm water as an ultrasound conducting medium. A sample holder box 4, made from a material transparent to ultrasound, and a slider 6 holding an ultrasound generating applicator (hereafter called simply an applicator or a transducer) so as to be slidable up and down, are mounted on supporting beam members 4a and 6a respectively, wherein beam members 4a and 6a are slidable to right and left. The entire system is aligned so that a sample in the sample box can be subjected to sonication in a far field of the ultrasound beam emitted from the applicator or transducer.

On the inner wall of the bath, except for a window (not shown) for visual observation of relative positioning of sample holder 4 and transducer 5, an ultrasound attenuating material 7, such as non-woven Nylon fiber adhering abrasive particles, is provided as a lining, so as to suppress reflected waves from the walls. Also, on the free water surface, floating sheets 8 made of expanded polystyrene, the underside of which is lined with the same attenuation material, are floated for suppressing reflections from the free water surface.

In the measurement for hemolysis, sample blood was taken from a vein of a male having heparin added thereto to prevent coagulation, and then cooled in a refrigerator. A sample of 1 ml was contained in a polyethylene sack having a 20 μ thick wall. The sample sack was housed in the sample box, dipped in the 36° C. bath water, sonicated for 30 min. at respective testing conditions (frequency and intensity) and then centrifuged. The obtained serum was checked for hemolysis by colorimetry and analysis of its LDH (lactate dehydrogenase) content.

It was confirmed that there exists a threshold intensity for the occurrence of hemolysis, that sonication is safe under the threshold (hereafter called the hemolysis limit), and that positive hemolysis took place above this limit.

A hemolysis threshold was found below 1000 mW/cm² at 24 kHz, 36 kHz, and 100 kHz, but no hemolysis was found at 1000 mW/cm² in a range of 160 kHz - 1 MHz.

Figure 2:
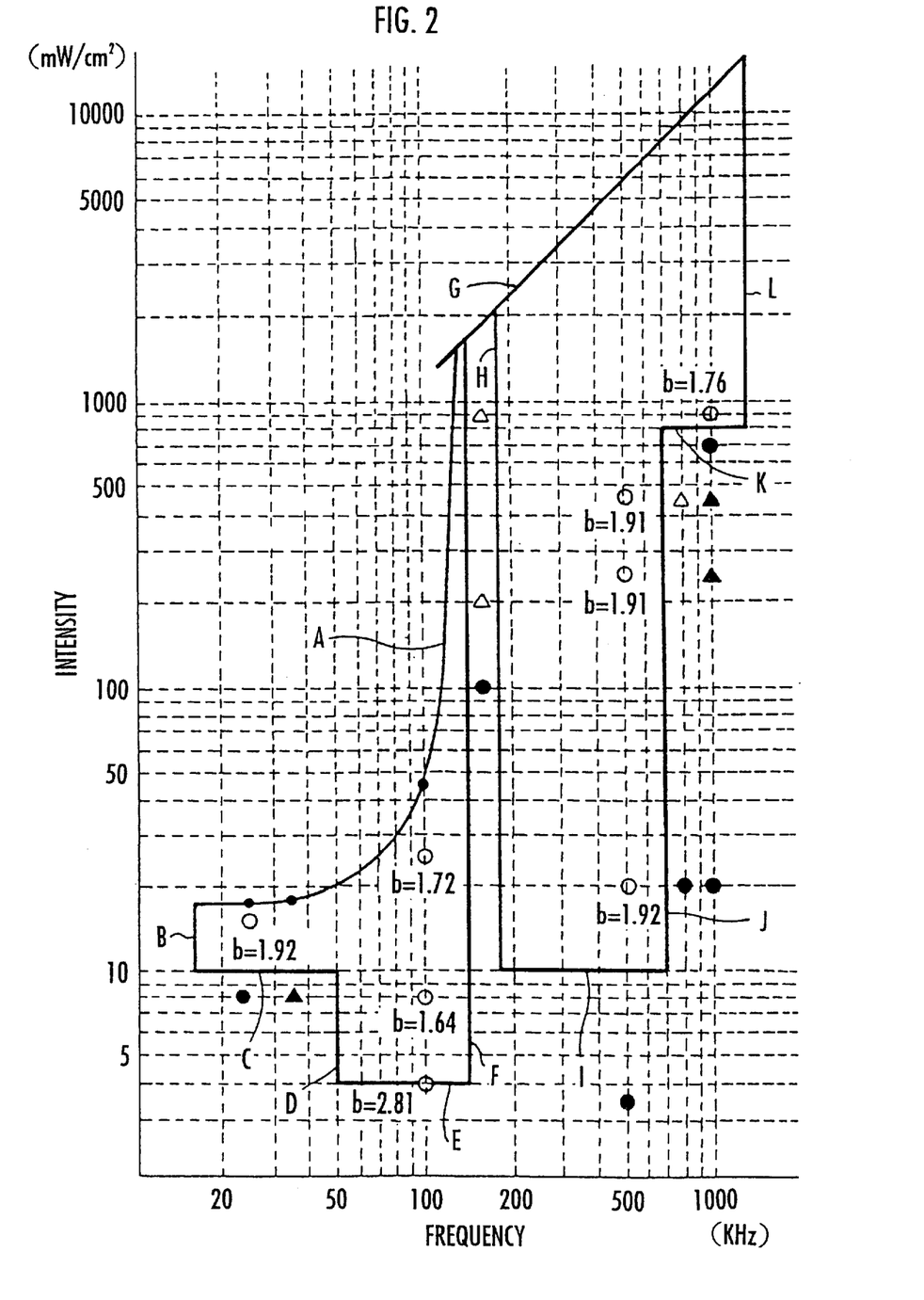
FIG. 2 is a graph showing the effective region in frequency and intensity domain scaled logarithmically on both axes.

The measured thresholds for hemolysis are shown in table 1 and plotted in FIG. 2.

A cavitation limit, as well as an emulsifying limit of intensity, is greater than the hemolysis limit, so it is considered enough to observe hemolysis. The intensity limit for destruction of adipocyte was also much greater and never observed below 1000 mW/cm².

Consequently, the intensity safety limit in the present invention is defined by the hemolysis limit when in a range of 24 kHz–100 kHz by, and when in a range of 160 kHz–1 MHz, for undefined healthy individuals, by the medical diagnostic safety limit of 1000 mW/cm² given by the Society for Ultrasound in Medicine, and for medical treatment, by the limit of MI=0.6 given by WFUMB (the line G in FIG. 2) as shown in the Table 1 and FIG. 2.

As seen in Table 1, it is clear that the 20–50 kHz at 100–500 mW/cm² region disclosed in the prior art of Tokukai Hei 3-123559 exceeds the hemolysis limit and is therefore dangerous.

TABLE 1

| Frequency | Intensity for Hemolysis limit | Intensity for MI = 0.6 |
|---|---|---|
| 24 kHz | 17 mW/cm² | |
| 36 kHz | 18 mW/cm² | |
| 100 kHz | 32 mW/cm² | |
| 160 kHz | | 1900 mW/cm² |
| 500 kHz | | 5800 mW/cm² |
| 1 MHz | | 11900 mW/cm² |
| 1.3 MHz | | 15500 mW/cm² |

Then, lipolysis for the various pairs of frequency and intensity were examined, within the safety region, for the aforesaid undefined healthy individuals. As a test animal, a rat was used. Its abdomen was subjected to sonication from the applicator, located at a distance such that an acoustic farfield having a uniform intensity distribution sufficiently widespread to cover the whole abdomen was established in a 36° C. water bath 2, as shown in FIG. 1.

The central nerves were anesthetized using Nembutal so that effects such as psychological stress, pain caused by blood sampling, and recognition of lower ultrasound frequencies which the rat might have sensitivity to hear, were cut off. Then, the abdominal hair was shaved to prevent air bubbles from collecting in them, and the rat's abdomen was washed with a surface active agent to make the surface hydrophilic.

Then, a "pre-sonication blood sample was taken from the tail vein and 10 minutes of sonication in the above-described manner was performed in the 36° C. water bath. After sonication, the rat was taken out of the bath into room air and left for 10 minutes.

Then, a "post-sonication blood sample was taken again from the tail vein. Both blood samples were centrifuged and their separated serum analyzed to determine quantitatively the content of FFA, a product of lipolysis, and compared with a control, which was processed similarly but without any sonication. The number of the tested samples was 15 for control, 6 for 24 kHz at 15 mW/cm , 8 for 500 kHz at 20 mW/cm², 12 for MHz at 900 mW/cm², and 4 for other frequency-intensity pairs.

When the FFA content before sonication is expressed by X and the content after sonication is expressed by Y, the increase (d=Y−X) shows no consistency or co-relation with sonic intensity, and most of the values were not significantly different from those of the control at student t test.

On the other hand, Y depends on X as if a certain slope or folding factor b (b=Y/X) may exist.

The points of the coordinates X and Y are scattered in the X-Y plain but are well regressed into a line passing through the origin of the X-Y coordinates. The slope b gives the multiplication factor or folding factor.

The slope b of the control was 1.24±0.109 and it was confirmed that the difference from b=1.04±0.09 of the non-processed control was due to the warm 36° C. water immersion.

The slope b at each point in the coordinates was compared with the slope b of the control at student t test.

At each point, it was judged whether it is effective or non-effective, considering together test t of b and d. The results are shown in FIG. 2 and classified by markings, wherein the various markings have meanings as shown in Table 2.

TABLE 2

| Mark | Final judgement | t test of b | t test of d |
|---|---|---|---|
| ○ | Effective | Significant | Significant |
| Δ | Not effective | Significant | Weakly insignificant |
| ▲ | Not effective | Significant | Strongly insignificant |
| ● | Not effective | Insignificant | Completely insignificant |

At each effective point in FIG. 2, the b value (folding factor) is shown together.

As seen from FIG. 2:

(A) There are effective regions in the lower frequency region of 15 kHz–140 kHz and higher frequency regions of 180–1.3 MHz.

(B) In each region, there is a lower threshold of intensity above which lipolysis was effective and under which it was not effective.

(C) Within the effective region, the folding factor was almost constant, b=1.94±0.16, and was not dependent on frequency nor intensity. In the lower intensity region, the folding factor was not significantly different from that of the control (b=1.24±0.109) and lipolysis was not effective.

(D) The lower effective limit was 10 mW/cm$^2$ within the higher frequency region such as 500 kHz, and 10 to 4 mW/cm$^2$ in the lower frequency region, dependent on frequency.

The facts shown above would give some suggestions on the mechanism of lipolysis, but at present precise details of the mechanism are still not clear.

Now, the effective regions are to be defined by drawing boundary lines considering the threshold points shown in FIG. 2.

Each mark shall be explicated region and is far from the boundary line.

○ exists in a perfectly effective region and is far from the boundary line.

● exists in a completely non-effective region and is far from the boundary.

Δ Δ exists almost on or very near to the boundary line.

▲ Δ exists near the boundary line but in a non-effective region.

Considering such explications, the effective regions were shown by way of the boundary lines appearing in FIG. 2.

Hereafter, the boundary lines shall be explained using English alphabetical characters indicated at each boundary point.

G. The effective upper boundary was set at an allowable level of the Mechanical Index, namely MI=0.6, according to WFUMB.

L. The boundary was set at a frequency of 1.3 MHz, where the effective depth disappears on the body surface for undefined healthy peoples. For treatment, a higher frequency with higher intensity to penetrate could be used. However, the power absorption is proportional to the squared frequency, and heating would become too much and might be dangerous by exceeding the Thermal Index. Thus, this region for treatment was excluded.

K. The point 800 kHz at 450 mW/cm was Δ (ineffective) and the point 1 MHz at 700 mW/cm$^2$ was ● (ineffective). Therefore, in a range of 700 kHz–1.3 MHz, the lower boundary was set at 800mW/cm$^2$ and upper boundary was set at the allowable MI level.

J. The point 800 kHZ at 450 mW/cm$^2$ was Δ and 800 kHZ at 20 mW/cm$^2$ was ● and points 500 kHz at 450, 250, 20 mW/cm$^2$ were ○, completely effective, and therefore the boundary was set at 700 kHz.

I. The point 500 kHz at 20mW/cm$^2$ was ○ and 500 kHz at 3.5mW/cm$^2$ was ●, so the middle point of 10 mW/cm$^2$ was set as a boundary.

H,F. The points 160 kHz at 900 mW/cm$^2$, 200 mW/cm$^2$ were Δ and the point 160 kHz at 100 mW/cm$^2$ was ●. As a non-effective frequency range could not result in a perfect line spectrum in physical or biochemical phenomenon, a width of ±20 kHz was added for the non-effective range, its lowest limit was set at 140 kHz and its highest limit was set at 180 kHz.

E. For 100 kHz at 4 mw/cm$^2$ was ○, completely effective. Therefore, the lowest limit would be still further lower. However, the effective depth became almost zero if such level was applied on the body surface. So, the lowest limit was set at 4 mW/cm$^2$.

D. At an intensity of 8 mW/cm$^2$, the point 100 kHz was ○ perfectly effective, the point 36 kHz was ▲ non-effective, and the point 24 kHz was ●. completely non-effective. Therefore, the boundary was set at 50 kHz which is near 36 kHz and between 24 kHz and 100 kHz.

C. The point 24 kHz at 8 mW/cm$^2$ was ●, completely non-effective. The point 36 kHz at 8 mW/cm$^2$ was ▲ non effective, and the point 24 kHz at 15 mW/cm$^2$ was ○, completely effective. Thus, the lower limit was set at the middle level of 10 mW/cm$^2$.

B. This is the lower limit at which ultrasound and further lower frequencies can be audible sometimes for certain people, resulting in undesirable noise.

A. This is the boundary of aforesaid hemolysis limit experimentally obtained by the inventors.

The effective regions formed by the aforesaid boundaries are shown in FIG. 2. The first aspect corresponds to the region enclosed by boundaries of A, B, C, D, E, and F. The second aspect corresponds to the region enclosed by the boundaries G, H, I, J, K and L.

Here, an evaluation of the prior art must be done, wherein the evaluation will be described as follows.

The reported result of the equipment for health and beauty is such that 900 mW/cm$^2$ at 1 MHZ was effective but 700 mW/cm$^2$ at 1 MHz was non-effective. Thus, the threshold is presumed to be 800 mW/cm$^2$. If the sonication intensity is assumed to be 1000 mW/cm$^2$ (for undefined healthy individuals) at the body surface, the effective depth until the intensity attenuates to 800 mW/cm$^2$ is 1.7 cm for fat and 0.9 cm for muscle, and cannot penetrate to the visceral fat which must be reduced for improvement of health of undefined healthy, but overweight, people.

Concerning the range of 1–3 MHz at 100–500 mW/cm$^2$ as disclosed in the prior art (Tokukai Hei 4-89058), at least the region of 1 MHz and below 700 mW/cm$^2$ was non-effective, as shown in FIG. 2. Generally speaking, in higher frequency regions, if it is attempted that the intensity increases at the body surface while aiming to keep a necessary intensity in the deep body, a danger of exceeding the safety level of the Thermal Index or of inducing a temperature rise at body surface may occur, as the energy (square of sound pressure) absorption per 1 cm is proportional to the squared frequency, and heat generated within 1 cm increases.

In conclusion:
1. As shown in FIG. 2, an effective and safe region lies in the frequency bands of 15 kHz–140 kHz and 180 kHz–1.3 MHz. The mechanism of each band would be different.
2. In the 15 kHz–140 kHz band, the attenuation coefficient is low and ultrasound energy can reach deep into the body, so it may be effective for lipolysis of not only subcutaneous fat but also of visceral fat. The latter is the cause of adult diseases.
3. In the 180 kHz–1.3 MHz band, the same effectiveness exists as in the effective intensity region. For example, at 500 kHz the same effectiveness (folding factor) exists within a wide intensity range of 10–1000 mW/cm$^2$. This means that it is suitable for lipolysis of a wide depth range from shallow to deep. Further, a merit is expected in that the intensity is attenuated so low in depth that undesirable effects on viscera or bone can be avoided.
4. A burning or consumption of the lipolysis product must be devised.

Figure 3:
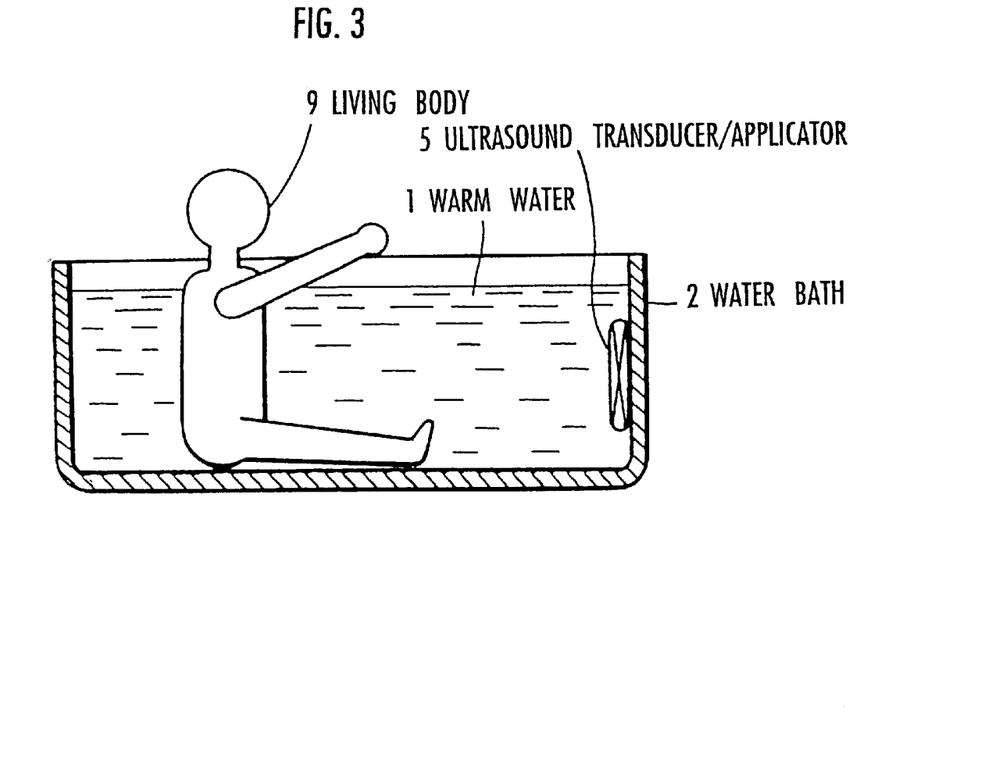
FIG. 3 is an illustrative cross-sectional view showing a first embodiment of the ultrasound sonication equipment of the present invention.

Next, the first embodiment of the equipment of the present invention is explained while referring to FIG. 3. The equipment is composed of a bath 2 and an ultrasound applicator 5 disposed on the wall of the bath 2. The applicator 5 generates ultrasound energy by applying a high frequency voltage fed from a non-illustrated driving circuit, and sonicates the body through the warm water 1. In the sonication equipment shown in FIG. 3, a macroscopic nearly uniform acoustic field is formed, even though there are speckle-like irregularities locally below the wave length due to multiple reflections from the walls. In the equipment, sonication of nearly the whole body is attained. If the intensity is near an upper allowable level, the walls should be made non-reflective and local irregularities due to standing waves should be avoided.

Next, a second embodiment of the equipment of the present invention is explained with reference to FIG. 4. The equipment is composed of water bath 10 containing warm water 1 and the ultrasound applicator 5 which is disposed on the bottom of the bath. A living body 9 contacts the warm water with a sponge provided as an elastic sealing member. At the bottom of the bath, a pipe 12 is provided to supply warm water 1 at constant pressure, wherein overflow is guided to the overflow container 13 through a non-illustrated overflow pipe, or alternatively, the water 1 penetrates through the sponge and is discharged out through the drain pipe 14. The applicator 5 generates ultrasound energy in a same manner as FIG. 3 and thereby sonicates the living body 6 through the warm water 1.

Figure 4:
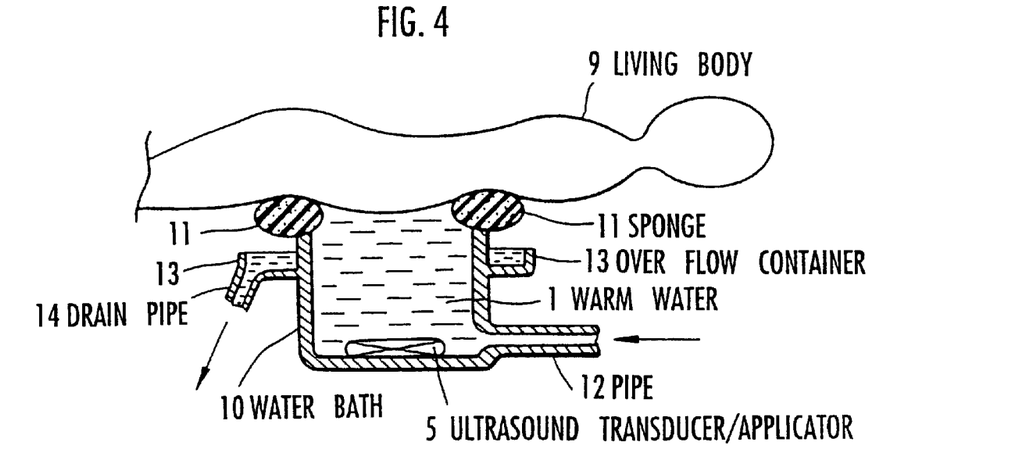
FIG. 4 is an illustrative cross-sectional view showing a second embodiment of the ultrasound sonication equipment of the present invention.

In the equipment shown in FIG. 4, the abdomen can contact an open water free surface without any air bubbles remaining.

It is desirable to monitor the water presence because transducers such as water-immersed types may be damaged by a lack of water. Such accidents can be detected by a change in the driving current of the transducer.

Figure 5:
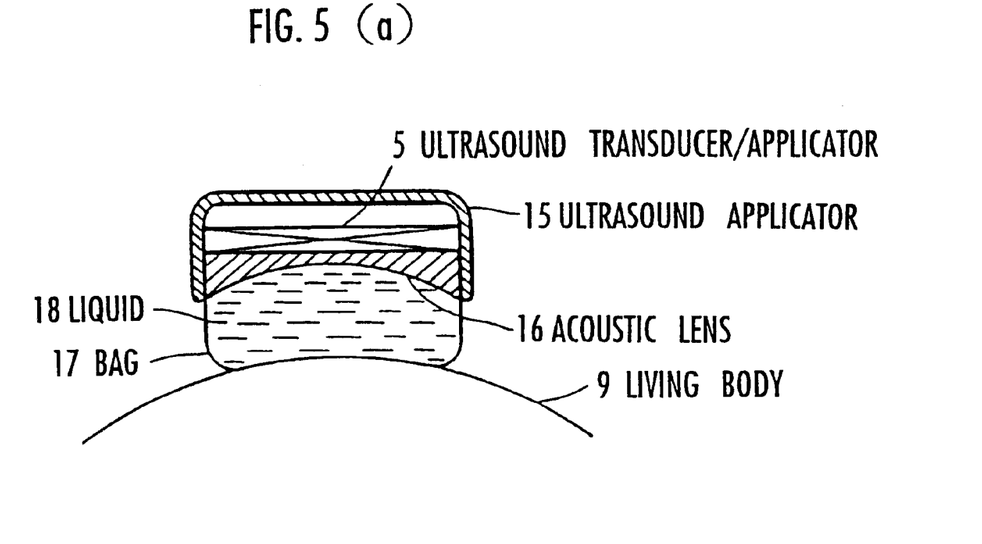
FIG. 5 is an illustrative cross-sectional view showing a third embodiment of the ultrasound sonication equipment of the present invention.

Next, the third embodiment of the equipment of the present invention is explained with reference to FIG. 5.

The sonication method of prior art provided scanning along the body surface area by using a small transducer and interposing an acoustic coupling agent such as jelly. This is reasonable because irregularity of the near field due to interference can be averaged by such area scanning. But, in this method, some caution is required whenever a very definite threshold exists as shown in the aforesaid hemolysis. There can be some dangerous cases, such that biological phenomenon may jump non-linearly at a localized spot over the threshold intensity, even though its mean is still below the threshold. Therefore, when the near field is used, a high mean value near an allowable limit cannot be used. The use of far field thus is a solution. Also, the small sonication area of such a small transducer forces the operator to scan manually over a wide area. This is yet another defect.

The ultrasound applicator 15 shown in FIG. 5(a) is composed of an ultrasound transducer 5, an acoustic lens 16 provided in front of the transducer 5, and a bag 17 made from an elastic material such as polyethylene and containing an ultrasound conducting material made up of a liquid 18 such as water or oil. The transducer 5 generates ultrasound energy, as explained in FIG. 3, and sonicates the body 9 through the liquid 18 and the bag window 17.

The aforesaid acoustic lens 16 is made from a sound conducting solid material having a faster sound velocity than the liquid 18, and contacts the transducer 5 on its upper surface. Its under surface is formed to be concave, to make the sound beam almost parallel by refraction at the boundary of the lens 16 and the liquid 18. It is also possible to form a converging beam by increasing the concave curvature, wherein an effect similar to that of the applicator 23, to be shown later in FIG. 6(c), is expected. The bag 17 and a sound conducting medium 18 such as water can easily deform and thereby fit to a curved surface of body 9 and so contacts well with the body 9. In the contact boundary between the bag 17 and body 9, a non-illustrated acoustic coupler (such as jelly) may interposed to exclude any air remaining between them.

The ultrasound applicator shown in FIG. 5(a) can be used for sonication in air, without using a water bath, and can be scanned along the surface of the body 9. Thus, it is suitable for localized sonication and is of a design having a fairly widespread sonication area.

The aforesaid acoustic coupler is used as an ointment on the body 9, and therefore can contain a percutaneous administrative agent for obesity reduction, such as capsaicine. The creamy agent of the aforesaid percutaneous administrative agent for obesity reduction can also prevent air from entering between the bag 17 and body 9. Therefore, it can be used as the acoustic (sound) coupler by itself, even if some deficiency in acoustic impedance matching may remain. Such an acoustic coupler, mixed with a percutaneous administrative agent for obesity reduction, or a newly developed acoustic coupler optimized so as to provide both an obesity reduction function and an acoustic coupling function, is very useful.

It should be noted that monitoring of any localized shortage of the aforesaid jelly is desirable whenever a wide area scanning along the surface of the body 9 is necessary.

The ultrasound applicator shown in FIG. 5(a) can be provided with a hand belt 20, as shown in FIG. 5(b), which is made of a synthetic resin or leather on an upper part thereof, so that the operator can easily handle the applicator by inserting his or her hand into the gap 21 between the belt 20 and the applicator 15.

Figure 6:
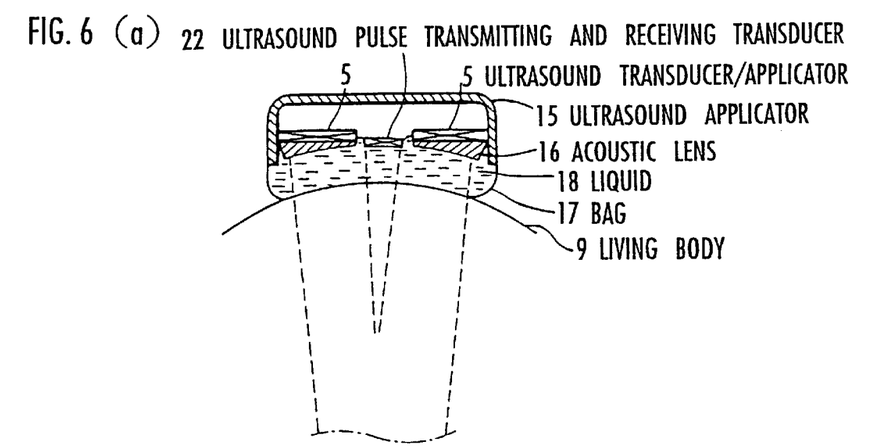
FIG. 6 is an illustrative cross-sectional view showing another example of the third embodiment of the ultrasound sonication equipment of the present invention.

Next, referring FIG. 6, another modified version of the ultrasound applicator shown in FIG. 5(a) shall be explained.

The ultrasound applicator shown in FIG. 5(a) has some possibility of causing adverse effects to the bone or to certain parts of viscera depending on its frequency, intensity and the point of sonication. Especially, bone is known to strongly absorb ultrasound energy, and is often heated to the point that some pain in the bone membrane occurs. On the contrary, for the fat-containing liver, it is requested to sonicate a specific organ. Therefore, there are many cases where the internal structure, or temperature rise, due to sonication should be considered.

As shown in FIG. 6(a) and FIG. 6(b), a part of the applicator 15 can be taken away so that an ultrasound pulse transmitting and receiving transducer can be provided instead of that part. FIG. 6(a) shows an example where the central part of the ultrasound transducer 5 is removed and an ultrasound pulse transmitting and receiving transducer 22 is provided. FIG. 6(b) shows an example where an end part of the ultrasound transducer 5 is removed and an ultrasound pulse transmitting and receiving transducer 22 is provided.

The ultrasound pulse transmitting and receiving transducer 22, in the applicator 15 shown in FIG.6(a) and FIG. 6(b), can be of a linear or of a sector scan array, as is known in conventional B-mode echo imaging equipment. It is possible to aim at the point to be sonicated, and to monitor temperature rise of the sonicated point, by constructing an image as a result of measuring such physical constants as the receiving time and the intensity of the reflected pulse wave, and by calculating the temperature with the temperature dependency of sound velocity or absorption, and the detected change of arrival time and intensity.

A sonication condition can be controlled by estimating the temperature rise of the sonicated part of the body, from the present intensity of penetration or reflection from the sonicated part, as compared with the initial intensity at the start of sonication, by utilizing the fact that ultrasound attenuation at the transmission of fat varies quite largely depending on temperature, such as 10% per degree near 20° C.

Further, as shown in FIG. 6(c), another ultrasound applicator 23, housing a pulse transmitting and receiving transducer 22, can be provided in addition to the two applicators 15, for monitoring the location, structure and temperature of the part where the two beams of the applicators 15 cross each other.

It is also possible to use the transducer for CW sonication, and also for pulse mode operation, by utilizing time-switching when a high frequency such as 500 kHz is used.

Further, as shown in FIG. 6(c), plural applicators can be used for generating a strong intensity field at a specific region, which is focused by crossing the applicator beams with each other by a specified angle θ by utilizing addition or interference. Further, by this means, it becomes possible to concentrate the intensity up to a necessary level onto a specific deep region, while keeping the intensity at each surface below an allowable level by plural sonications aimed at a specific region from applicators located at different positions of the body surface.

Such a means can solve problems such as over-intensity at each surface, caused by increasing intensity to overcome attenuation on the way to a specific deep region, and is especially effective for sonication of deep regions using a high frequency but high attenuation such as 1–1.3 MHz.

Further, by modifying the arrangement shown in FIG. 6 (c) so that the pulse or impulse waves from each of the transducers, placed along the same wave propagation axis and facing to each other, can cross at θ=180°, it becomes possible to provide a strong local effect on a small specified region. In this case, it is possible to adjust the location and area of the specific region to be sonicated by changing the angle θ of intersection, the number of sound beams, namely, transducers and/or reflectors, and also by shifting or adjusting the respective frequency and/or its phase.

In the case of low frequency sonication, the attainable depth within the body is lengthened, whereas in high frequency treatment, the attainable depth is shortened due to higher attenuation at high frequencies.

In the low frequency region, effects such as macroscopic deformation, agitation and fluidization are to be expected. In the higher frequency region, effects such as hormone release by sonication on sympathetic nerves, microscopic agitation or fluidization of the phospholipid membrane of the oil droplet, or of the membrane at ends of the sympathetic nerves can be expected.

Such effects are not yet proven at present, but their character of effect must be different from each other. In order to utilize these effects together, it is possible to provide plural applicators in the equipment and to transmit different frequencies of ultrasound, alternatively or simultaneously. An alternative frequency change can be accomplished also by exchanging different frequency transducers.

Figure 7:
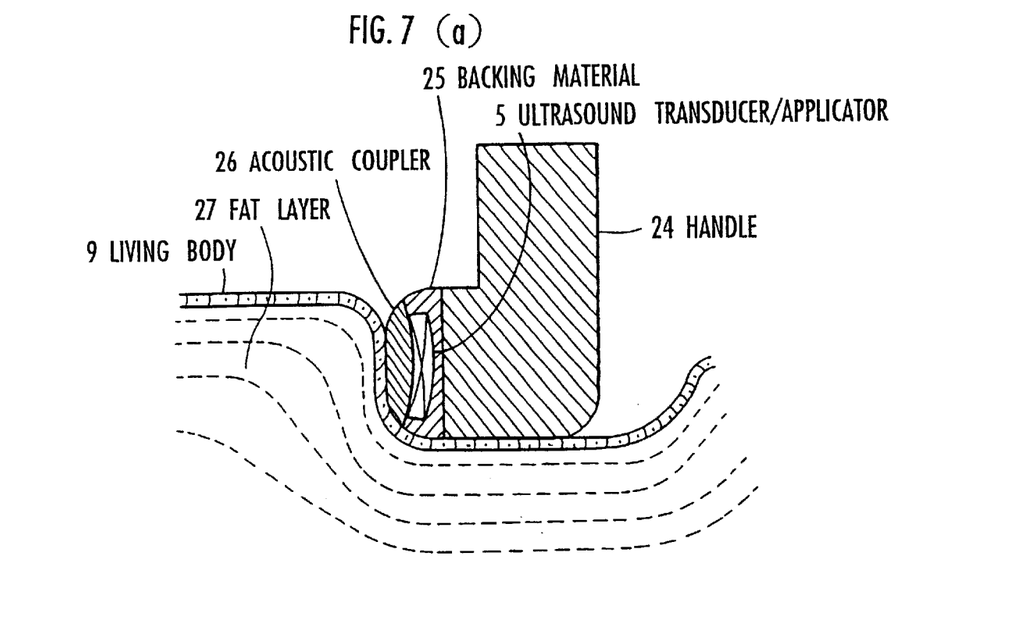
FIG. 7 is an illustrative cross-section view showing a fourth embodiment of the ultrasound sonication equipment of the present invention.

Next, the forth embodiment of the equipment of the present invention is explained with reference to FIG. 7.

Ultrasound applicators a, b, and c shown in Fig, 7 are composed of a ultrasound transducer 5, a backing material 25, a hard acoustic coupler 26 and variously angled handles 24. The ultrasound applicators can be used for scanning a specific area of the body surface by contacting directly with interposing a sound coupler such as jelly. These types of applicators are suitable for high frequency small transducers such as 500 kHz.

In the applicators shown in FIG. 7(a), it becomes possible to sonicate a subcutaneous fat layer mainly by pressing the front part of the L-shaped handle against the body surface strongly and deforming the body surface shape, as shown in FIG. 7(a), where 9 is the skin of a human and 27 is a fat layer.

The applicators shown in FIG. 7(a) are thus suitable for parts of the body having large amounts of subcutaneous fat, such as the breech area, and are characterized by application of sonication toward the subcutaneous fat layer with the ultrasound transducer 5 from a part of a concave deformed body surface, by strongly pressing the coupler 26 located at the end of handle 24 onto the skin 9 and the subcutaneous fat layer 27. For easy operation of this type of sonication, the center line of handle 24 and the direction of sonication are constructed perpendicular to each other.

The acoustic or sound coupler 26 is provided between the concave transducer 5 and the body skin 9, for matching the transducer 5 with the body and also for ease of handling.

Also, a sound coupler such as jelly is interposed between the coupler 26 and the body surface. The sonication can be, for example, of 500 kHz at 1000 mW/cm$^2$ for 10 min. Such a sonication time can be controlled by a timer.

The handle 24 can be of straight stick shape, as shown in FIG. 7(b), or of an obliquely extending stick from the backing 25, as shown in FIG. 7(c). The shape of the handle can be selected for easier handling depending on the part of body and the operator Next, the fifth embodiment of the equipment of the present invention is explained with reference to FIG. 8. In the ultrasound applicator shown in Fig, 8, an ultrasound transducer 5 is housed in a shower head 28 and imposes ultrasound energy into the water or warm water 30 in the shower head 28. The water is supplied from a hose 29. The ultrasound-imposed water 30 flows out in a collection of many small stream jets through the small holes 31 provided at the front face of the shower head 28 for striking against a non-illustrated body surface part.

Figure 8:
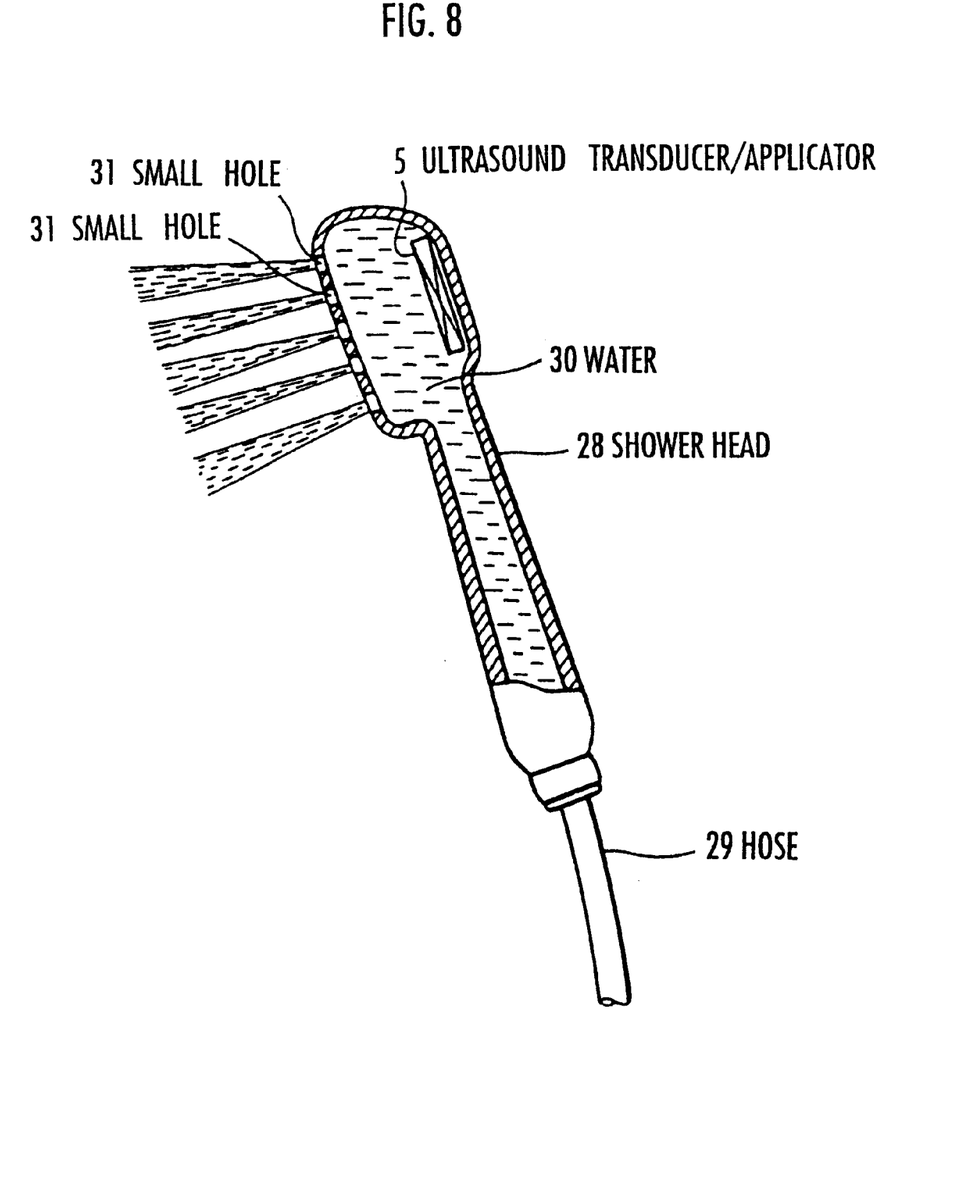
FIG. 8 is an illustrative cross-sectional view showing a fifth embodiment of the ultrasound sonication equipment of the present invention.

Accordingly, when the jet streams are poured onto a body part to be sonicated, such as the abdomen, thigh, etc., sonication becomes easier and more adaptive to any part of body. The ultrasound-imposed water 30 can also be poured as large diameter stream per se, without dividing into many small streams by the small holes 31.

The lipolysis products generated by the aforesaid ultrasound sonication equipment shown in aforesaid embodiments must be burned or consumed. Otherwise, a reverse synthetic process synthesizes them to fat and again stores them within an adiopocyte. Therefore, it is important to burn the FFA (Free Fat Acid) by physical exercise or dietary control etc.

In this aspect, a synergistic effect can be expected by combining ultrasound sonication together with administering an obesity reducing agent or medicine. For example, such a combination can prevent fat moving from the peripheral area to the locally sonicated and fat reduced area, and hence local fat reduction can be realized easier while an effect on beauty is enhanced.

Such an obesity reducing agent or medicine is under development within wide and various aspects. Appetite suppressers, digestion/uptake suppressers, energy consumption enhancers, thermogenesis enhancers, etc. are known, and other hormonal research aiming at the promotion of lipolysis or suppression of lipo-synthesizing are also known. Central nervous system appetite suppressers such as catecholamine, norepinephrine, dexfenfluamin, dopamine, serotonin, and transmittal nerve appetite suppressers such as amphetamine, mazindol, are known. Sibutramine is another known as appetite suppresser and thermogenesis enhancer. Orlistat is known as a digestion/uptake supressant. In addition, there are leptine, neuropeptide Y suppressers, CCK-A promoters, butabinzide, bromocryptine suppressing lipo-synthesizing, insulinotropine enhancing concentrations of insulin in the blood, triglytazone for promoting consumption of glucose, cytokine adjusters for controlling cytokine activity which is known as an information transmitter between cells, along with teaoph, caffeine, and theophylline which are contained in tea. As methods of administration, there are oral, percutaneous, injective, and inhalative administrations.

The combination of sonication and the administration of a thermogenetic and body temperature-rising food or medicine is synergistically effective. As a temperature rise is caused from the burning of FFA, such temperature rise increases the radiation of body heat outwardly and promotes consumption of FFA, namely through Lipolysis. Such foods and medicines can comprise capsaicin contained in red pepper, mustard, etc., or Hydroxytoric acid contained in garcinia (fruit). A thermometabolic (thermogenestic) enhancer can be a beta3 receptor controller such as BRL26830A, BRL35135, CL316,243, or Sibutramine.

FFA can be consumed by providing a cooling means and immersing parts of the body such as the hand, foot within the cooling means which is kept at a temperature of 24° C. or by exposure to a shower of at a temperature of around 24° C. Such a cooling procedure can be performed either on, before or after sonication.

For cooling, a sound conducting media as shown in FIG. 6 etc. can be used under a cooled condition. Other means, such as providing a temperature controlling means for controlling the temperature of the warm water 1 in the bath 2 of FIG. 3 or bath 5 of FIG. 4, to attain a temperature which is lower than body temperature, such as 24–29° C., can be used. Such temperature controlling can be performed by connecting a small flexible tube for conducting the waters out of the bath 3 in FIG. 3, or bath 5 in FIG. 4, and the water bags 17 in FIGS. 5 and 6, to the aforesaid controlling means. Body heat is thereby taken away at the contacting surface with the cooled media. Then, thermogenesis is induced autonomically by the homeostasis of the living body to keep the body temperature constant, whereby FFA is exhausted.

The additional embodiment will be explained. In FIG. 6(c), the third embodiment uses plural ultrasound transducers, but reflectors can replace some of the transducers. Such a combination makes it possible to adjust the used frequency and or phase, by detecting the frequency and/or phase of the received reflected waves on the transmitter, and by controlling the location, number and intensity of the standing wave. Generally, the operating frequency of transducer can be varied by ±10% from the center (or resonant) frequency. Defining the sonication region becomes possible by controlling the standing wave.

By not only utilizing the reflector but also by utilizing an absorber, such region defining becomes possible. A certain number of absorbers, the shape of which is formed appropriately and made from an absorbing material, such as a mixture of heavy particles and a visco-elastic substance, can be used for this purpose. Moreover, by cyclically varying the frequency and/or phase and intensity with time, scanning or moving of the region of interest in a body, and flattening of a speckle-like intensity field of the sonicated region by time-meaning during the time-cycle can be expected.

INDUSTRIAL APPLICABILITY

It becomes possible by the present invention to provide an equipment for performing lipolysis of living body fat effectively, safely and in a short time by sonicating ultrasound to living body.

The equipment can accomplish fat reduction easier, more effectively, and faster than the reduction by exercise or diet alone. Benefits on the treatment and prevention of the diseases originated from obesity, and the improvement of health and enhancement of beauty are very great, and the demand for this type of equipment is very large.

Accordingly, this equipment is expected to generate a significant industry and its industrial applicability is great.

What is claimed is:

1. An ultrasound sonication equipment comprising an ultrasound generating means and means for sonicating a living body for performing lipolysis, and wherein said equipment produces a generated ultrasound defined such that its frequency is in the range of 15–140 kHz, wherein the intensity when in a range of 15–50 kHz is greater than 10 mW/cm$^2$ and lower than the hemolysis limit, and wherein the intensity when in a range of 50–140 kHz is greater than 4 mw/cm$^2$ and lower than the hemolysis limit or safety level based on the Mechanical Index.

2. An ultrasound sonication equipment comprising an ultrasound generating means and a sonicating means for application of ultrasound energy to a living body for performing lipolysis, and wherein said equipment produces a generated ultrasound defined such that its intensity when in a range of 50–140 kHz is greater than 4 mW/cm$^2$ and lower than the hemolysis limit or safety limit for the diagnosic ultrasound equipment.

3. An ultrasound sonication equipment comprising an ultrasound generating means and a sonicating means for application of ultrasound energy to a living body for performing lipolysis, and wherein said equipment produces a generated ultrasound defined such that its frequency is in the range of 180–1.3 MHz, wherein the intensity when in a range of 180–700 kHz is greater than 10 mW/cm$^2$ and lower than the safety level based on the Mechanical Index, and wherein the intensity when in a range of 700–1.3 MHz is greater than 800 mW/cm² and lower than the safety level based on the Mechanical Index.

4. An ultrasound sonication equipment comprising an ultrasound generating means and a sonicating means for application of ultrasound energy to a living body for performing lipolysis, and wherein said equipment produces a generated ultrasound defined such that its frequency is in the range of 180–1.3 MHz, wherein the intensity when in a range of 180–700 kHz is greater than 10 mW/cm² and lower than the safety level based on diagnostic ultrasound equipment, and wherein the intensity when in a range of 700–1.3 MHz is greater than the 800 mW/cm² and lower than the safety level based on diagnostic ultrasound equipment.

5. The aforesaid ultrasound sonication equipment according to claim 1, 2 or 3, charaterized in that the intensity safety level is defined by a Mechanical Index of 0.6.

6. The aforesaid ultrasound sonication equipment according to claims 1, 2, 3 and 4, characterized in that a monitoring means is provided for monitoring the location or temperature of the sonicated region.

7. The aforesaid ultrasound sonication equipment according to claim 1, 2, 3 or 4, characterized in that an acoustic conducting medium is provided, for delivering the generated ultrasound to the living body.

8. The aforesaid ultrasound sonication equipment according to claim 7, characterized in that the ultrasound conducting means comprises an acoustic coupling agent interposed between the conducting means and the body.

9. The aforesaid ultrasound sonication equipment according to claim 8, characterized in that the acoustic coupling agent contains an obesity reducing substance or medicine therein.

10. The aforesaid ultrasound sonicaiton equipment according to claim 1, 2, 3 or 4, characterized in that a means is provided for pouring an ultrasound-imposed liquid onto the living body.

11. The aforesaid ultrasound sonication equipment according to claim 1, 2, 3 or 4, characterized in that the means are provided for administering an agent or medicine for the reduction of obesity.

12. The aforesaid ultrasound sonication equipment according to claim 1, 2, 3 or 4, characterized in that a cooling means is provided for cooling at least a part of the living body undergoing a course of sonication.

13. The aforesaid ultrasound sonication equipment according to claim 12, characterized in that a cooling means is provided for cooling the acoustic medium.

* * * * *